(12) United States Patent
Thun et al.

(10) Patent No.: US 9,689,788 B2
(45) Date of Patent: Jun. 27, 2017

(54) METHOD FOR MEASURING FINE PARTICULATES AND FINE PARTICULATE SENSOR FOR DETERMINING THE PARTICLE SIZE OF FINE PARTICULATES

(71) Applicant: Hella KGaA Hueck & Co., Lippstadt (DE)

(72) Inventors: Carsten Thun, Bremen (DE); Thomas Niemann, Delmenhorst (DE); Ole Morisse, Bremen (DE); Alexander Gohmann, Bremen (DE)

(73) Assignee: HELLA KGAA HUECK & CO., Lippstadt (DE)

( * ) Notice: Subject to any disclaimer, the term of this patent is extended or adjusted under 35 U.S.C. 154(b) by 0 days.

(21) Appl. No.: 15/055,046

(22) Filed: Feb. 26, 2016

(65) Prior Publication Data
US 2016/0252452 A1   Sep. 1, 2016

(51) Int. Cl.
| | |
|---|---|
| *G01J 5/02* | (2006.01) |
| *G01N 15/14* | (2006.01) |
| *G01N 15/06* | (2006.01) |
| *G01N 15/02* | (2006.01) |
| *G01N 15/00* | (2006.01) |
| *B60S 1/08* | (2006.01) |

(52) U.S. Cl.
CPC ..... *G01N 15/1434* (2013.01); *G01N 15/0211* (2013.01); *G01N 15/0227* (2013.01); *G01N 15/06* (2013.01); *G01N 15/1459* (2013.01); *B60S 1/0862* (2013.01); *G01N 2015/0026* (2013.01); *G01N 2015/0693* (2013.01); *G01N 2015/1454* (2013.01); *G01N 2015/1486* (2013.01); *G01N 2015/1493* (2013.01)

(58) Field of Classification Search
CPC ....... G01N 2021/9586; G01N 21/3554; G01N 2021/435
See application file for complete search history.

(56) References Cited

U.S. PATENT DOCUMENTS

| | | | |
|---|---|---|---|
| 5,451,931 A | 9/1995 | Muller et al. | |
| 5,455,675 A * | 10/1995 | Witt | G01N 15/0211 356/336 |
| 5,703,568 A | 12/1997 | Hegyi | |

(Continued)

FOREIGN PATENT DOCUMENTS

| | | |
|---|---|---|
| DE | 4130586 A1 | 3/1993 |
| DE | 19530289 A1 | 2/1997 |

(Continued)

*Primary Examiner* — Kiho Kim
(74) *Attorney, Agent, or Firm* — Muncy, Geissler, Olds & Lowe, P.C.

(57) ABSTRACT

In a method for measuring fine particulates in the vicinity of a motor vehicle with an optical receiving device, at least one LED (2, 3) arranged inside the motor vehicle lights up an outside air region. The optical receiving device is designed to capture the area under examination in a spatially localized manner and takes an intensity measurement in an area that is lit by the LED. The intensities measured are analyzed for diffraction patterns that depend on the size of the fine particulates. Additionally, a portion of the light that is coupled into the windshield is also analyzed for the presence of water on the windshield.

14 Claims, 3 Drawing Sheets

(56) References Cited

U.S. PATENT DOCUMENTS

| | | | |
|---|---|---|---|
| 5,917,603 A * | 6/1999 | Tanaka | B60S 1/0822 |
| | | | 356/343 |
| 5,991,049 A * | 11/1999 | Tanaka | B60S 1/0822 |
| | | | 356/328 |
| 6,084,519 A | 7/2000 | Coulling et al. | |
| 6,108,084 A | 8/2000 | Winner | |
| 6,118,383 A | 9/2000 | Hegyi | |
| 2014/0321701 A1 | 10/2014 | Halimeh et al. | |

FOREIGN PATENT DOCUMENTS

| | | | |
|---|---|---|---|
| DE | 102012210116 A1 | 12/2012 | |
| FR | GB 1247470 A * | 9/1971 | ......... G01N 15/0205 |
| WO | WO 98/51549 A1 | 11/1998 | |

* cited by examiner

METHOD FOR MEASURING FINE PARTICULATES AND FINE PARTICULATE SENSOR FOR DETERMINING THE PARTICLE SIZE OF FINE PARTICULATES

BACKGROUND OF THE INVENTION

Field of the Invention

The invention relates to a method for measuring fine particulates in the vicinity of a motor vehicle with an optical receiving device. The invention further relates to a fine particulate sensor for determining the particle size of fine particulates for a motor vehicle with an optical system.

Brief Discussion of the Related Art

Fine particulate sensors, in which a sample space inside a housing is tested with an optical system are known. In this context, active ventilation must be carried out and/or the sample space must be cleaned repeatedly to remove residues from the sample space.

SUMMARY OF THE INVENTION

The object underlying the invention is to provide a largely maintenance-free method for measuring fine particulates.

This is achieved with a method having the features of patent claim 1 and with a fine particulate sensor having the features of patent claim 8. Advantageous variations of the invention are described in the subordinate claims.

In a method using an optical receiving device for measuring fine particulates in the vicinity of a motor vehicle, it is provided as essential to the invention that at least one LED arranged inside the motor vehicle lights up an outside air region through a windscreen of the motor vehicle, that the optical receiving device is designed to capture the area under examination in a spatially localised manner, takes an intensity measurement in an area lit by the LED, and that the intensities measured are analysed for diffraction patterns that depend on the size of the fine particulates. Further according to the invention, at least some of the radiation emitted by the at least one LED is reflected on the windscreen, and the light reflected by the windscreen is received and analysed with regard to wetting the windscreen with drops of water. A particularly maintenance-free measurement may be carried out with such a method, since the sample space is not defined by a housing, but instead is realised as the intersection between the area lit by the LED and the area captured by the optical receiving device. In this context, fine particulates are typically defined as dust or particles with a size <2.5 µm. If such particles are illuminated by a LED, diffraction patterns are created. At the same time as the light emitted by the LED or the electromagnetic radiation emitted by the LED, an analysis is also carried out to determine whether there are water droplets on the windscreen. Some of the emitted light is coupled into the windscreen and is reflected multiple times therein. If the windscreen is wetted with water droplets, a portion of the light that has been coupled into the windscreen is decoupled, so that the intensity of the light is attenuated in this way after it has been reflected multiple times in the windscreen. A sensor combining two functions may thus be incorporated in a single unit. By virtue of its multiple use of individual components, the sensor may be of particularly compact and economical construction. A LED is preferably used that is in the infrared range, that is to say with a wavelength in the range from 780 nm to about 1000 nm for example. It is particularly preferable if two LEDs with different wavelengths are used. This enables the accuracy of the measurement to be increased further. The two LEDs preferably both emit infrared radiation, but preferably on wavelengths at least 100 nm apart. For example, one LED may emit in the 800 nm range, and the other LED in the 900 nm range.

In a preferred variant, the angle between the primary maximum and the first order maximum of the diffraction pattern is calculated. This angle is directly proportional to the size of the fine particulates. The amplitude of the first order maximum is proportional to the number of particles. If matter or dust particles of different sizes are present, different diffraction patterns are superimposed on each other, and these must be detected and evaluated correspondingly. Consequently, if LEDs with different wavelengths are used, more data is generated, for a more accurate analysis.

The LEDs are preferably directed toward a region in front of the windscreen. Thus, the method is conducted on a purely optical basis, and does not require a housing to define the sample space, and in this respect does not use a housing. Alternatively, the outside air in the flow channel of the vehicle's fresh air intake may be captured.

In a preferred variant, the light reflected by the windscreen is also received by the optical receiving device, which is also used to measure the intensities of diffraction patterns caused by the fine particulates. In this way, the receiving device can also be put to multiple uses. This enables the sensor to be of particularly compact and inexpensive design. In another development of the invention, either the LED that emits the electromagnetic radiation or also multiple LEDs and/or the receiving device may be switched on or off in at alternating points in time, so that receiving for analysis of diffraction patterns for fine particulates is carried out at one point in time and evaluation of the reflected light with regard to wetting of the windscreen is carried out at another point in time. In this way, the measurement may be controlled particularly reliably by the parallel analysis. Alternatively, an arithmetical reconciliation may be carried out so that the percentages that are attributable to the respective other measurement can be calculated out from the measured results.

With regard to equipment, the object is solved with a fine particulate sensor for determining the particle size of fine particulates for a motor vehicle with an optical system, in which according to the invention the fine particulate sensor has at least one LED, which lights up an area of outside air, that the fine particulate sensor has an optical receiving device that is designed to receive an area lit by the LED in a spatially localised manner, and that the fine particulate sensor has an analysis device that analyses the intensities measured by the receiving device for diffraction patterns, which depend on the size of the fine particulates. The fine particulate sensor according to the invention is also integrated in a rain-light sensor. In this context, preferably at least one LED fulfils a dual function or at least one optical system fulfils a dual function, in other words the LEDs used are focussed by an optical system to emit electromagnetic radiation. The electromagnetic radiation that is bundled in this way is used both to determine the particle size of the fine particulates and as a rain-light sensor in the measurement in which light is reflected by the windscreen. With such a fine particulate sensor, a low-maintenance fine particulate sensor is created with a freely defined sample space, which is not delimited by a housing. The idea of measuring fine particulates in a motor vehicle is to be interpreted in this context such that the method steps are carried out at least in part components that are present in the motor vehicle. The actual measurement takes place outside the motor vehicle, so it is air, in particular air from outside the motor vehicle, that is analysed with respect to fine particulates. In a particularly preferred variant of the invention, a central receiving device and a plurality of LEDs surrounding the optical receiving device in a ring are used. This ensures that a particularly high degree of accuracy is achieved.

Preferably, two LEDs are provided. They preferably have wavelengths in the infrared range, which are preferably about 100 nm apart and in the range between 780 and 1400 nm. One LED preferably has a wavelength range between 780 and 850 nm, and a second LED is in the wavelength range between 900 and 1000 nm.

In a particularly preferred variant, the LEDs and the optical receiving device are aligned on a common sample space. The intersection between the one or two LEDs and the optical receiving device defines the sample space.

In another preferred variant, the fine particulate sensor is integrated in another sensor. This may preferably be a rain-light sensor or an air quality sensor for example. Preferably, at least one LED uses the optical system present in these sensors. Particularly when a rain-light sensor is used, one or preferably two LEDs use an optical system of the rain-light sensor. In addition, a second optical system of the rain-light sensor is preferably used by the optical receiving device.

The optical receiving device may be for example a camera system, or preferably a CMOS linear image sensor. Alternatively, the optical receiving device may also be a diode array. The diffraction pattern is reproduced particularly well in a diode array.

BRIEF DESCRIPTION OF THE DRAWINGS

In the following, the invention will be explained in greater detail with reference to a preferred embodiment thereof represented in the drawing. In particular, the drawing shows diagrammatically in.

DETAILED DESCRIPTION OF THE PREFERRED EMBODIMENTS

Figure 1:
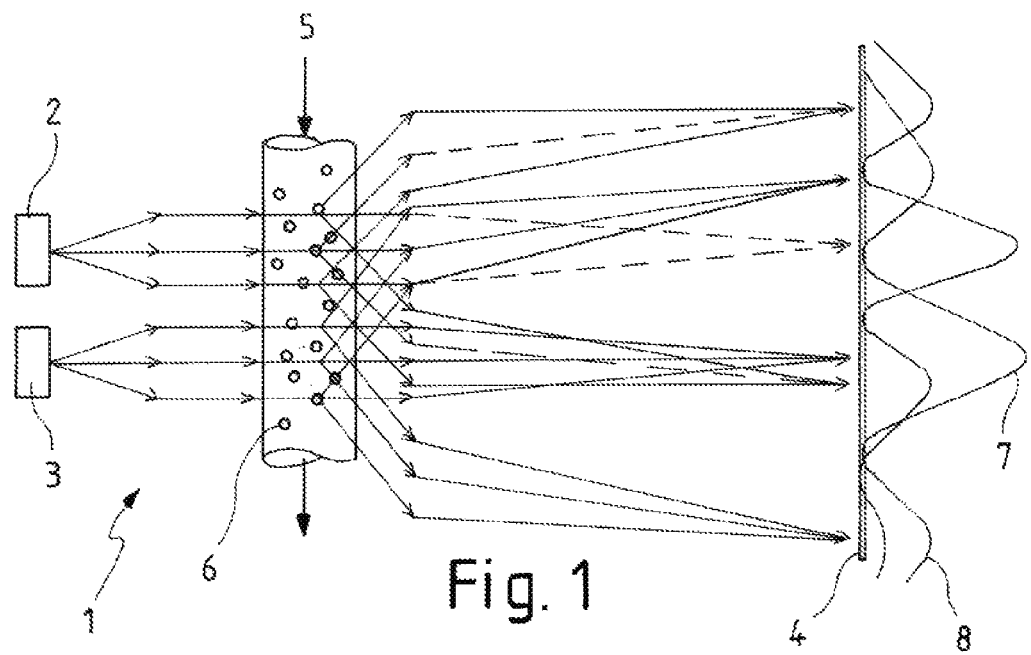
FIG. 1: a schematic representation of the measurement principle.

FIG. 1 is a schematic representation of a fine particulate sensor 1. The sensor comprises a first LED 2 and a second LED 3. Said LEDs emit electromagnetic waves in the infrared range. The first LED 2 preferably emits electromagnetic waves with a wavelength of about 820 nm and the second LED 3 preferably emits electromagnetic waves with a wavelength of about 940 nm. The electromagnetic waves are radiated into a sample space 5 that contains fine particulates 6. The electromagnetic waves are scattered by the particulates. The light is diffracted by small particles. This results in interference patterns with light and dark concentric rings. The angle of diffraction and the distances between the rings depend on the size of the particle. In this way, particles with a diameter of <2.5 µm can be differentiated from larger particles. The intensity of the rings is in turn proportional to the particle concentration, so that a quantitative analysis can also be made. The diffraction pattern is recorded by an optical receiving device 4, for example a CMOS linear image sensor or a corresponding camera. Here, a primary maximum 7 and a first order diffraction maximum 8 are shown. Different particle sizes result in different maxima, as is represented here by a first order diffraction maximum 9 of a different particle size.

Figure 2:
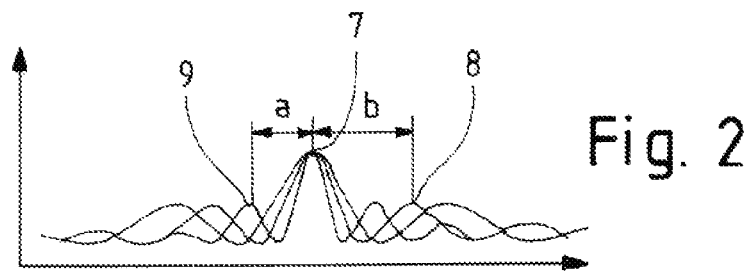
FIG. 2: a schematic view of a mapping image.

This is also represented again in FIG. 2 as a graph of intensity on the Y-axis against the angle of diffraction along the X-axis. Compared with primary maximum 7 first order diffraction maxima 8 and 9 are visible. The angle between the first order diffraction maximum and the primary maximum is directly proportional to the particle size. The amplitude is proportional to the particle concentration. Because of the various particle sizes, an intersection is formed by various maxima, which must be identified.

The use of two LEDs 2 and 3 generates more data, from which a more accurate analysis can be derived.

Figure 3:
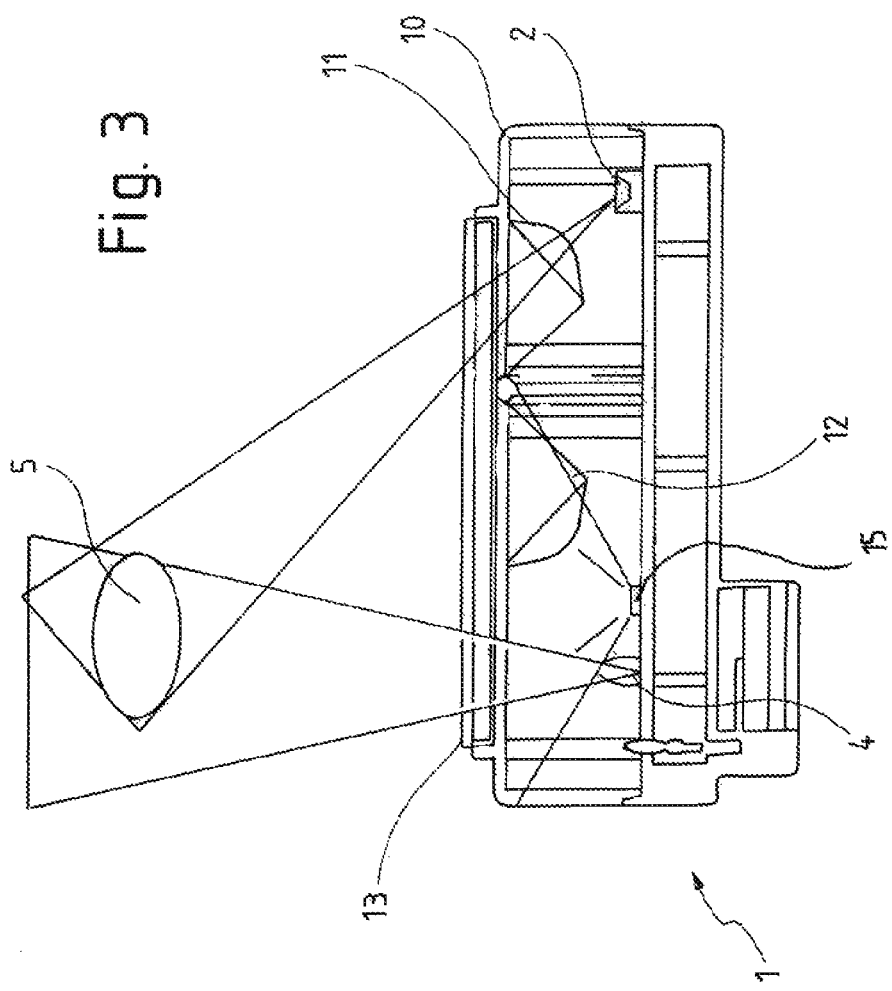
FIG. 3: a first possible embodiment of a fine particulate sensor according to the invention.

FIG. 3 shows a first embodiment of a fine particulate sensor according to the invention. Fine particulate sensor 1 is arranged in a housing 10, which also accommodates a rain-light sensor. The rain-light sensor is arranged below a windscreen 13. The rain-light sensor comprises in particular optical systems 11 and 12, via which the electromagnetic waves are coupled into windscreen 13, where they are partially reflected before being decoupled again. The light that is reflected in windscreen 13 is guided through an optical system toward a receiver diode 15, by which it is received. The intensity measured there can then be used to determine whether and to what degree the windscreen is wetted with water droplets. In the example shown, optical system 11 is used by an LED 2. Said LED emits electromagnetic waves in the infrared range through optical system 11 into an area in front of windscreen 13. The field of view of an optical receiving device 4 is also directed toward this area, so that a sample space 5 is formed in the intersection area. The values detected by optical receiving device 4 are then analysed with regard to diffraction patterns in the manner described with reference to FIG. 2.

Figure 4:
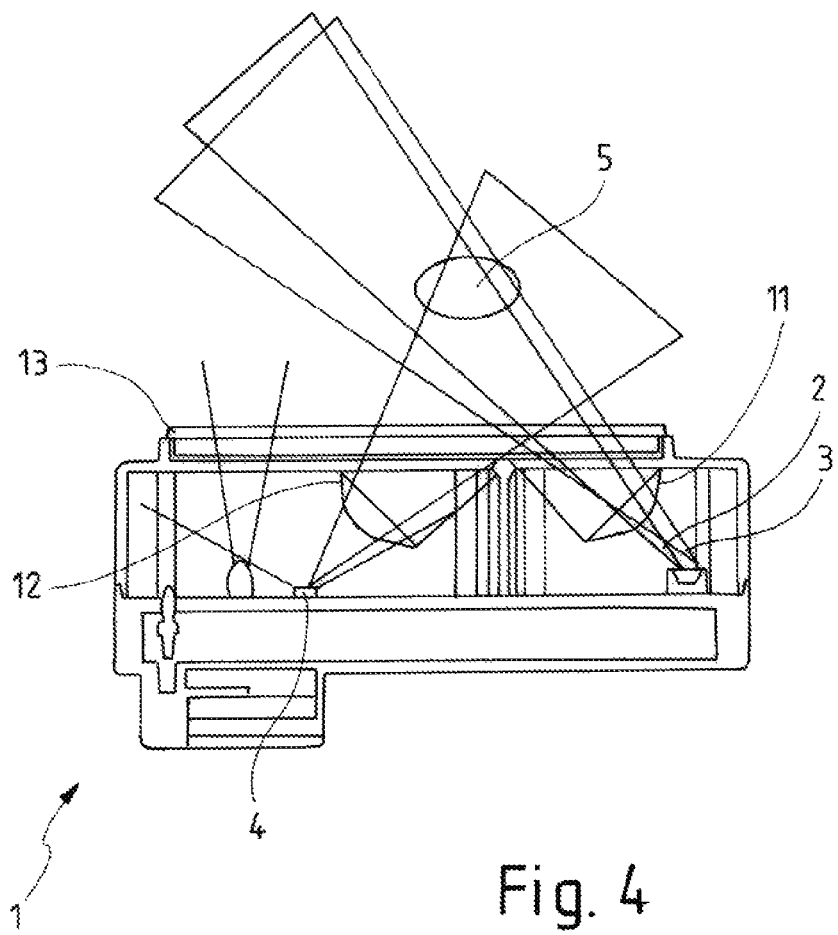
FIG. 4: a second possible embodiment of a fine particulate sensor according to the invention.

FIG. 4 represents a second embodiment of a fine particulate sensor 1 according to the invention. Here too, fine particulate sensor 1 is integrated in a rain-light sensor with a housing 10 and optical systems 11 and 12. In this case, both a first LED 2 and a second LED 3 are arranged below optical system 11 and both use optical system 11, so that the electromagnetic waves emitted by said LEDs 2 and 3 are radiated in an area in front of the windscreen. In this case, the optical receiving device 4, particularly the CMOS linear image sensor, is arranged below the second optical system 12. Sample space 5 is defined in the intersection area of the electromagnetic waves emitted by LEDs 2 and 3 and the area captured by optical receiving device 4. This is located in front of windscreen 13.

All of the features described in the preceding description and in the claims can be combined in any permutation with the features of the independent claim. The disclosure of the invention is thus not limited to those combinations of features that are described and/or claimed, but rather all combinations of features that reasonable within the scope of the invention are to be considered disclosed.

The invention claimed is:

1. A method for measuring fine particulates in the vicinity of a motor vehicle with an optical receiving device, wherein at least one LED arranged inside the motor vehicle lights up an outside air region through a windscreen of the motor vehicle, the optical receiving device is designed to capture the area under examination in a spatially localised manner and takes an intensity measurement in an area that is lit by the LED, the intensities measured are analysed for diffraction patterns that depend on the size of the fine particulates, the radiation emitted by the at least one LED is reflected at least in part by the windscreen, and the light reflected by the windscreen is received and analysed for wetting of the windscreen by water droplets.

2. The method according to claim 1, wherein two LEDs light up the outside air region with different wavelengths in the infrared range.

3. The method according to claim 1, characterised in that the LED radiates into an area in front of a windscreen.

4. The method according to claim 1, wherein the angle between the primary maximum and the first order maximum in the diffraction pattern is analysed.

5. The method according to claim 1, wherein the amplitude of the first order maximum is analysed with regard to particle concentration.

6. The method according to claim 1, wherein the light reflected by the windscreen is also received with the optical receiving device, which is also used to measure the intensities of the fine particulate diffraction patterns.

7. The method according to claim 6, wherein the LEDs and/or the receiving device are switched on or off in at alternating points in time, so that receiving for analysis of diffraction patterns for fine particulates is carried out at one point in time and evaluation of the reflected light with regard to wetting of the windscreen is carried out at another point in time.

8. The fine particulate sensor according claim 6, wherein at least one LED uses an optical system present in the rain-light sensor.

9. A fine particulate sensor for a motor vehicle having an optical receiving device, wherein the fine particulate sensor comprises at least one LED which lights up an area of outside air, the optical receiving device is designed to capture an area that is lit by the LED in spatially localised manner, the fine particulate sensor comprises an analysis device for analysing the diffraction patterns recorded by the optical receiving device, and the fine particulate sensor is integrated in a rain-light sensor.

10. The fine particulate sensor according to claim 9, wherein the fine particulate sensor comprises two LEDs.

11. The fine particulate sensor according to claim 9, wherein the LEDs and the optical receiving device are directed toward a sample space.

12. The fine particulate sensor according to claim 9, wherein two LEDs use a first optical system and that the optical receiving device uses a second optical system.

13. The fine particulate sensor according to claim 9, wherein one central receiving device and a plurality of LEDs surrounding the optical receiving device in a ring formation are provided.

14. A motor vehicle having a windshield and a rain-light sensor with a housing and optical systems arranged behind the windshield that are directed toward the windshield, wherein a fine particulate sensor according to claim 9 is integrated in the rain-light sensor.

* * * * *